United States Patent [19]

Hannah

[11] 4,376,774

[45] Mar. 15, 1983

[54] ANTIBIOTIC N-HETEROCYCLYL THIENAMYCIN

[75] Inventor: John Hannah, Matawan, N.J.

[73] Assignee: Merck & Co., Inc., Rahway, N.J.

[21] Appl. No.: 43,087

[22] Filed: May 29, 1979

[51] Int. Cl.³ .................... A61K 31/44; C07D 401/14
[52] U.S. Cl. .................................... 424/263; 424/251;
424/270; 424/272; 424/273 R; 544/319;
544/320; 544/324; 544/327; 544/330; 546/112;
546/138; 546/183; 546/272; 548/159; 548/181;
548/213; 548/214; 548/222; 548/246; 548/306;
548/318
[58] Field of Search ........................ 546/272; 424/263

[56] References Cited

U.S. PATENT DOCUMENTS 3,950,357   4/1976   Kahan et al. .................. 424/271 X
4,150,145   4/1979   Christensen et al. .......... 546/272 X
4,235,920  11/1980   Christensen et al. .......... 546/272 X

FOREIGN PATENT DOCUMENTS 848545   5/1977   Belgium .

OTHER PUBLICATIONS

Brown, A., et al., *J.C.S. Chem. Comm.*, 1977, 523–525.
Doub, L., in *Medicinal Chemistry*, vol. V, John Wiley and Sons, New York, 1961, pp. 350–353, 362–369 and 410–411.
Northey, E., *The Sulfonamides and Related Compounds*, Reinhold Pub. Corp., New York, 1948, pp. 377–379.
March, J., *Advanced Organic Chemistry*, 2nd Ed., McGraw Hill, New York, 1977, p. 598.

*Primary Examiner*—Richard A. Schwartz
*Attorney, Agent, or Firm*—F. M. Mahon; J. A. Arno; H. J. Pfeiffer

[57] ABSTRACT

This invention relates to a new class of thienamycins (I) and their pharmaceutically acceptable salts and esters which are useful as antibiotics:

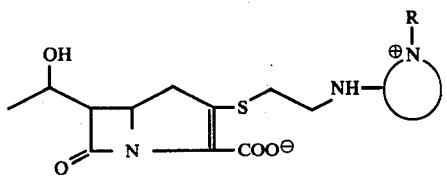

wherein the stylized radical (hereafter referred to as R'):

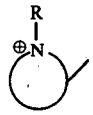

attached to the amino nitrogen group of thienamycin represents a mono- or polycyclic N-containing heterocyclic group; R is, inter alia, hydrogen, substituted and unsubstituted: alkyl, aryl, alkenyl, heterocyclylalkenyl, aralkenyl, heterocyclylalkyl, aralkyl, —NR$_2$, COOR, CONR$_2$, —OR, or CN.

4 Claims, No Drawings

ANTIBIOTIC N-HETEROCYCLYL THIENAMYCIN

BACKGROUND OF THE INVENTION

This invention relates to a new class of thienamycins (I) and their pharmaceutically acceptable salts and esters which are useful as antibiotics:

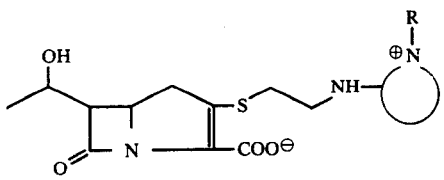

wherein the stylized radical (hereafter referred to as R'):

attached to the amino nitrogen group of thienamycin represents a mono- or polycyclic N-containing heterocyclic group; R is, inter alia, hydrogen, substituted and unsubstituted: alkyl, aryl, alkenyl, heterocyclylalkenyl, aralkenyl, heterocyclylalkyl, aralkyl, —$NR_2$, $COOR$, $CONR_2$, —$OR$, or $CN$. The heterocyclic radical R', is further defined below.

Thienamycin and all of its isomers are known and are described by structure 1, below. In this regard, reference is made to U.S. Pat. No. 3,950,357 issued Apr. 13, 1976 which is directed to thienamycin and to co-pending, commonly assigned U.S. patent application Ser. No. 17,680 filed Mar. 5, 1979 which is directed to the total synthesis of thienamycin and all of its isomers. To the extent that the cited patent and application provides starting materials for the practice of the present invention, they are incorporated herein by reference.

The compounds of the present invention are most conveniently isolated as the zwitterionic species demonstrated by structure I.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli, Pseudomonas, Proteus morganii,* Serratia, and Klebsiella. Further objects of this invention are to provide chemical processes for the preparation of such antibiotics and their non-toxic pharmaceutically acceptable salts and esters; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are prepared by reacting thienamycin (1) with a chosen electrophilic N-heterocyclic reagent (2 or 3) calculated to provide the species of the present invention I. The following reaction diagram conveniently summarizes this process and introduces the precise identity of such electrophilic reagents and the nature of the products of this reaction (I, above).

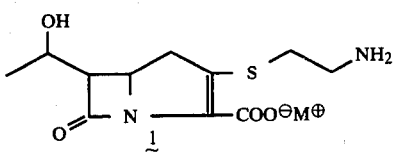

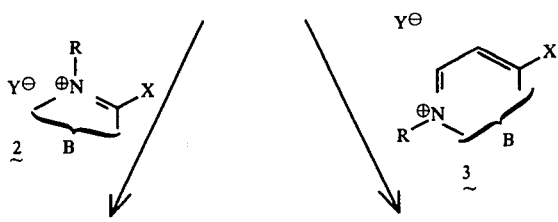

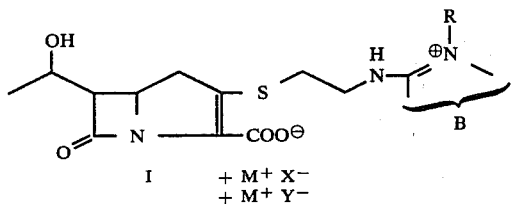
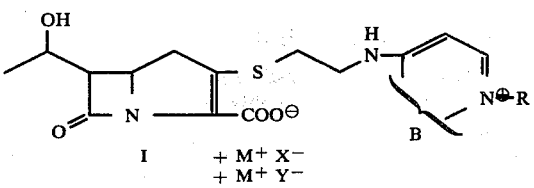

-continued wherein:

B is, inter alia, the residue of a 5-, o a 6-membered aromatic heterocycle; or a 5,5-, 6,5-; or 6,6-bicyclic aromatic heterocycle; wherein the additional ring atoms are chosen either entirely as carbon, or include one or more atoms selected from S, N and O. The caron and nitrogen atoms of any such ring may carry substituents such as substituted and unsubstituted: alkyl and alkenyl having 1–6 carbon atoms, phenyl, phenylalkyl having 1–6 carbon atoms in the alkyl moiety, 5- or 6-membered heterocyclyl wherein the hetero atom or atoms are selected from O, N or S, —OR$_2$, —NR$_2$, —COOR, —CONR$_2$, —CN, halo, —SR, —SO.R$_3$, —SO$_2$R, —NHCONH$_2$, —SO$_3$R, —SO$_2$NR$_2$ (R is defined immediately below),

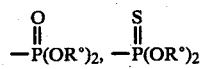

(R° is hydrogen or alkyl having 1–6 carbon atoms); wherein the substituent or substitutents are selected from halogen such as chlorine or fluorine, hydroxyl, phenyl, alkyl, alkoxyl, carboxyl and phenylalkyl (each alkyl having 1–6 carbon atoms);

R is selected from H; substituted and unsubstituted: alkyl having 1–10 carbon atoms, alkenyl having 2–10 carbon atoms, phenyl, phenylalkyl, phenylalkenyl having 7–12 carbon atoms, 5- or 6-membered heterocyclalkyl wherein the hetero atom or atoms are selected from O, N or S and the alkyl has 1–6 carbon atoms, NR$_2$, OR, COOR, CN, and CONR$_2$ (R is defined here); wherein the substituent or substituents on R are selected from halogen such as chloro and fluoro, hydroxyl, OR, NR$_2$, COOR, CONR$_2$, CN,

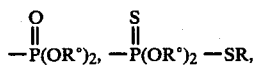

—SO.R, —SO$_2$R, (R° is hydrogen or alkyl having 1–6 carbon atoms), and alkyl having 1–6 carbon atoms;

R and B together may be joined to yield 6,5- and 6,6-bicyclic heterocycles in which the N$^\oplus$ is at a bridgehead;

X is a leaving group such as halogen, preferably fluorine; other leaving groups include: OCH$_3$, SCH$_3$; OSO$_2$OCH$_3$ OSO$_2$OCF$_3$,

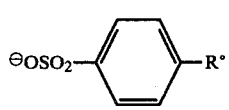

(R° is hydrogen or C$_{1-6}$ alkyl)

Y is a non-critical counter anion and representatively is: Cl$^\ominus$, Br$^\ominus$, I$^\ominus$,

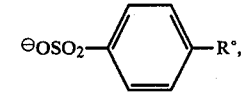

$^\ominus$OSO$_2$OR°, BF$_4{}^\ominus$, ClO$_4{}^\ominus$ and the like; wherein R° is H, loweralkyl or phenyl;

M$^\oplus$ is H, or an alkali or alkaline earth metal cation such as Na$^+$ or K$^+$, a tertiary amine salt, or the like;

In general words relative to the above reaction diagram, thienemycin (1) or a salt thereof in a solvent such as water at pH 7 to 8, tetrahydrofuran (THF), dimethylformamide (DMF) or the like or aqueous mixtures thereof (ideally such nonaqueous systems contain a base such as triethylamine, methyldiisopropylamine, or the like, to neutralize the acid HX produced by the addition/elimination reaction) is treated with a stoichiometric to four-fold excess of the illustrated electrophilic reagent (2 or 3) calculated to provide the desired product. Typically, the reaction is conducted at a temperature of from 0° to 40° C. and is accomplished within 1 to 5 hours. As demonstrated by the following examples, there are no undue criticalities in the parameters of reaction. More specifically, relative to the above reaction scheme, a set of representative conditions may be recited to illustrate a convenient preparation of the compounds of the present invention (I); such recitation, however, is solely for purposes of demonstration and is not to be construed as introducing any undue criticalities of reaction.

Standard Reaction Conditions

Using a pH meter coupled to an automatic burette containing 1.0 to 2.5 N aqueous sodium hydroxide, a magnetically stirred solution of thienamycin (1) in water is adjusted to pH 7 to pH 7.5 at 20° C.

The heterocyclic reagent (stoichiometric to twofold excess) is dissolved in water at 20° C. and added to the above solution. Alkali is automatically added to maintain the selected pH in the range 7 to 7.5, the rate of addition being a measure of the extent of reaction. The reaction may also be monitored by removing aliquots at timed intervals for analysis. A particularly suitable analytical scheme is liquid chromatography, for example, high pressure liquid chromatography (HPLC) over a reverse phase column of octadecylsilane (ODS) bonded to silica, using a U.V. detector and aqueous THF (tetrahydrofuran) solution (1 to 30%) as the mobile phase.

The reaction typically takes from 15 minutes to 5 hours at 20° C. The resulting reaction solution at pH 7 is worked up by partition chromatography over a column of Amberlite XAD-2 resin, eluting with aqueous THF solutions (up to 20%) and monitoring the fractions by HPLC as above. However, with the increasing availability of large scale ODS silica columns, the preferred method of product isolation is by preparative reverse phase HPLC directly on the reaction solution at the zwitterionic pH. The appropriate fractions are combined, evaporated to small volume and lyophilized to yield the product, which is conveniently characterized by I.R., U.V., N.M.R., and analytical HPLC.

In certain cases, the products are sufficiently insoluble in water to separate from the reaction solution at pH 7, and may be isolated simply by filtration.

Finally, a special circumstance should be mentioned. In the basic reaction, first described, the condensation of the thienamycin starting material and the reagent of choice does not occur readily when the group R, attached directly to the ring nitrogen of the reagent is hydrogen. In such circumstance, it is preferred to employ a quaternized ring nitrogen prior to reaction. The quaternizing group may be removed after the amino heterocycle bond has been formed to yield species of the present invention, I, wherein R is hydrogen:

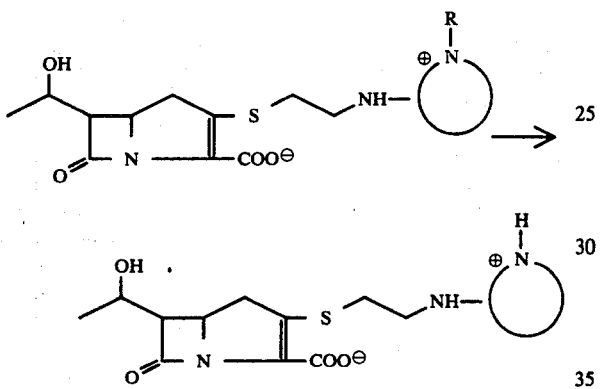

wherein R is —CH$_2$OCH$_3$, —CH$_2$OCOCH$_3$ or the like. According to the above scheme, Ic→Id, the group R is conveniently removed by treating Ic in anhydrous sulpholane at 20° C. with a 4- to 5-fold molar ration of ISi(CH$_3$)$_3$, followed by hydrolysis to yield Id. In the following diagram, R' is representatively illustrated as pyridyl:

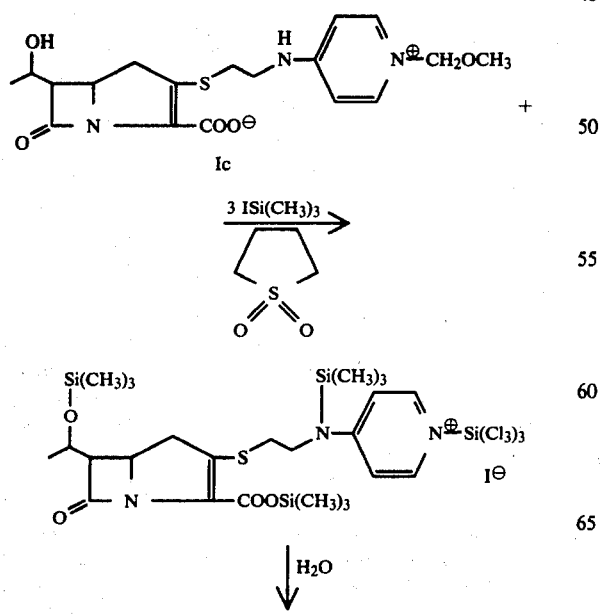

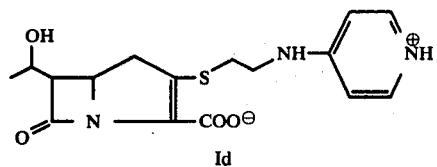

Id

The product Id is then isolated directly from the reaction solution at pH 6–7 by preparative reverse phase HPLC as already described.

IDENTIFICATION OF REAGENTS

The necessary electrophilic, N-heterocyclic reagents 2 and 3 are known and commercially available or may be prepared according to known procedures; see, for example: *Advances in Heterocyclic Chemistry*, pp. 1–56, Vol. 3 (1964) and pp. 71–121, Vol. 22 (1978); Academic Press. The following list representatively illustrates such reagents.

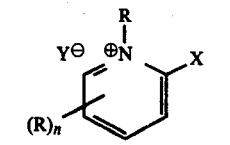

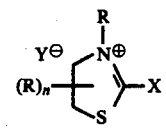

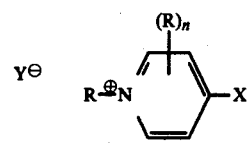

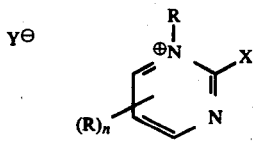

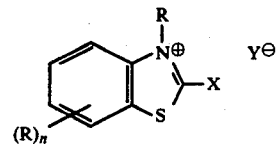

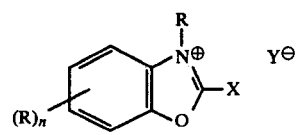

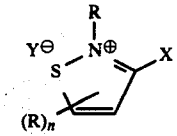

-continued

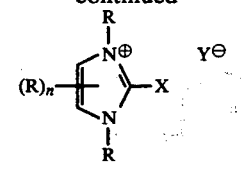

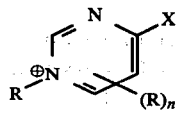

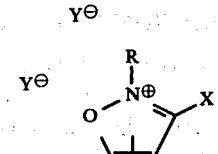

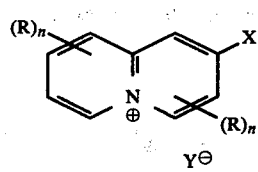

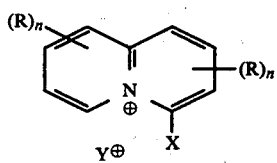

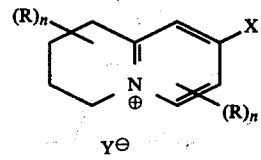

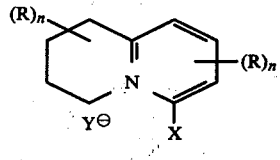

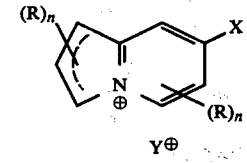

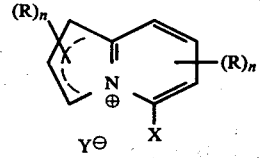

wherein all symbols have previously been defined; the dotted line indicates both saturated and unsaturated rings.

Relative to the above-listed reagents, the preferred values for the radical R which is directly attached to the ring nitrogen atom are: hydrogen; loweralkyl having from 1-10 carbon atoms; substituted alkyl wherein the substituent is chloro, fluoro, hydroxyl, alkoxy, substituted alkoxy, carboxyl, amino, sulfo and mono- and dialkylamino wherein each alkyl has 1-6 carbon atoms; phenylalkyl (alkyl moiety having 1-6 carbon atoms) and substituted phenylalkyl wherein the substituents are selected from chloro, fluoro, carboxyl, amino, hydroxyl, lower alkoxyl having from 1-6 carbon atoms, sulfo

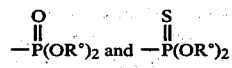

(R° is hydrogen or alkyl having 1-6 carbon atoms). The quinolizinium and indolizinium examples are a special category of preferred values of R, in that R is there an integral part of a bicyclic system (R', defined above).

The preferred values for the other, non-position-specific ring substituent R are: chloro, fluoro, carboxyl and loweralkyl having from 1-6 carbon atoms; substituted lower alkyl wherein the substituent is carboxyl cyano, alkoxyl having 1-6 carbon atoms, phenyl, and phenyloxy; the preferred value for n is 0 or 1. The preferred leaving group X is chloro or fluoro.

The compounds of the present invention (I) are valuable antibiotics active against various gram-positive and gram-negative bacteria and accordingly find utility in human and veterinary medicine. Representative pathogens which are sensitive to antibiotics I include: *Staphyloccus aureus, Escherichia, coli, Klebsiella pneumoniae, Bacillus subtilis, Salmonella typhosa,* Psuedomonas and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycine; lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure zwitterionic compound in sterile water solution or in the form of a soluble powder intended for solution. The pH of such solutions typically will correspond to the zwitterionic point; however, consideration of individual properties of solubility and stability may require such aqueous solutions to have a pH other than that of the zwitterionic point, for example in the range of 5.5 to 8.2.

The following examples, illustrate but do not limit the product, process, compositional or method of treatment aspects of the present invention. All reaction temperatures are in °C.

Finally, attention is drawn to a co-pending U.S. patent application Ser. No. 34,035 of John Hannah which was filed 4-27-1979. Such pending Hannah application is directed to 7-N-heterocyclylcephalosporins which are in analogy to the thienamycin compounds of the present invention. Thus, to the extent that the identified application recites common procedures and starting materials, it is hereby incorporated by reference.

EXAMPLE 1

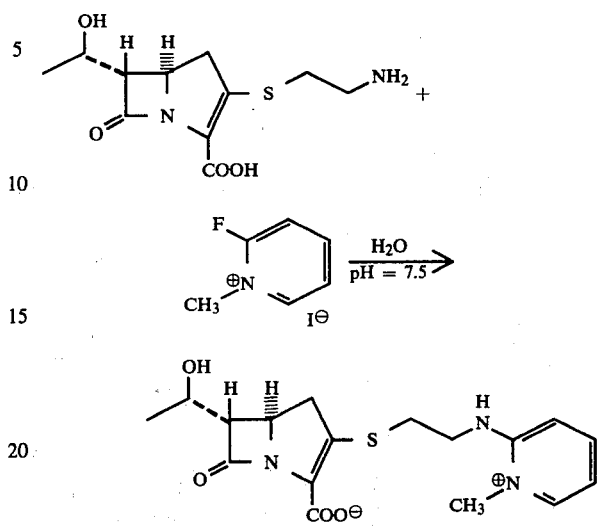

Thienamycin (91 mg., 0.334 mmole) is dissolved in distilled deionized water (2.5 ml) at 25° and the solution titrated to pH 7.5 with aqueous 1.0 N NaOH using an automatic burette. With vigorous magnetic stirring, 2-fluoro-1-methylpyridinium iodide (96 mg, 0.401 mmole) is added dissolving rapidly and causing instant response from the automatic burette to maintain pH 7.5. The progress of the reaction is monitored at timed intervals by removing aliquots for analytical HPLC over a Waters Associates $\mu C_{18}$ ODS reverse phase column with aqueous 10% tetrahydrofuran as the mobile phase, using a U. V. (254 nm) detector. After 40 minutes at 25°, the reaction solution is titrated to pH 6.0 and is put on a 3×44 cm column of Amberlite XAD-2 resin, prepared in distilled, deionized water, eluting with the same solvent, water. With the flow rate set at 2 drops per second, individual fractions of 200 drops each are collected, again using a U.V. monitor and analytical HPLC to locate the desired product. The eluting solvent is changed to aqueous 1% tetrahydrofuran at fraction 50 and to aqueous 2% tetrahydrofuran at fraction 75. The product is found in fractions 118–138 which are combined (140 ml) and lyophylized to yield a pale yellow powder (63 mg).

IR: β-lactam at 1764 cm$^{-1}$.

U.V.: $\lambda_{max}$ (H$_2$O) 198; 233; and 305 nm (25,180; 13,300; and 14,960 respectively).

NMR (300 MHz) (D$_2$O): δ1.26 (d, 3H, J=6 Hz, CH$_3$-9); 3.04–3.27 (m, 4H, CH$_2$-4 and CH$_2$-11); 3.36 (dd, 1H, J=2.8 and 6 Hz H$_6$); 3.78 (t, 2H, J=6 Hz, CH$_2$-12); 3.82 (s, 3H, N$^\ominus$-CH$_3$); 4.12 (m, 1H, H$_5$); 4.22 (m, 1H, H$_9$); 6.96 (dd, 1H, J=7 and 7 Hz, H$_5$, ); 7.24 (d, 1H, J=9 Hz, H$_3$,); 7.96 (m, 2H, H$_4$, and H$_6$,).

EXAMPLE 2

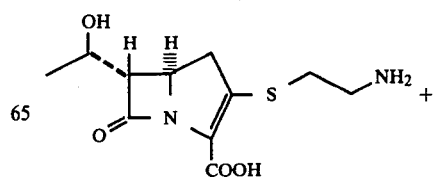

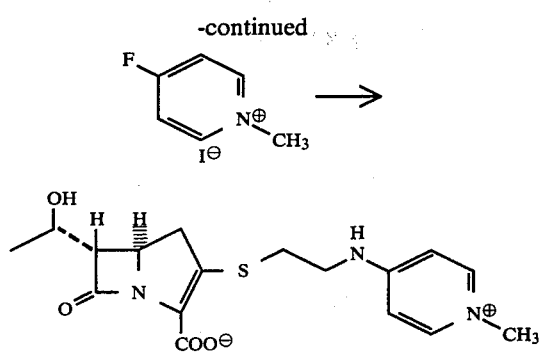

Following the procedure of Example 1, the above-indicated product is obtained when an equivalent amount of 4-fluoro-1-methylpyridinium iodide is substituted for 2-fluoro-1-methylpyridinium iodide.

IR.: β-lactam at 1761 cm$^{-1}$.

U.V.: $\lambda_{max}$ (H$_2$O) 198; 211; and 281 nm.

NMR: (300 MHz) (D$_2$O): δ1.24 (d, 3H, J=6 Hz, CH$_3$-9); 2.97–3.31 (m, 5H, CH$_2$-4; CH$_2$-11; and H$_6$); 3.67 (m, CH$_2$-12); 3.87 (s, 3H, N$^\ominus$-CH$_3$ 4.07 (m, 1H, H$_5$); 4.18 (m, 1H, H$_9$.)

EXAMPLE 3

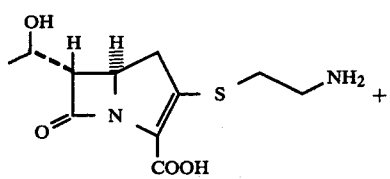

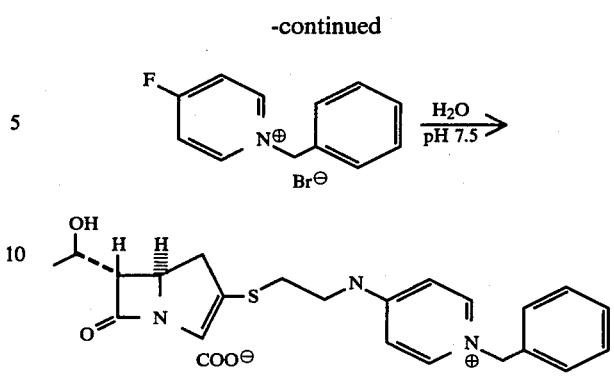

Following the procedure of Example 1, the above indicated product is obtained when an equivalent amount of 1-benzyl-4-fluoropyridinium bromide is substituted for 2-fluoro-1-methylpyridinium iodide.

EXAMPLE 4

Following the procedure described in the foregoing text and Examples, the following compounds listed in Table I are obtained. In Table I, appropriate remarks ae entered to signal any departure from established procedure. Also listed under "Remarks" in Table I are the necessary reagents.

TABLE I

| Compound | R' | Remarks |
|---|---|---|
| 1 | ▷—CH$_2$—N$^\oplus$⟨pyridinium-CH$_3$⟩ | ▷—CH$_2$—N$^\oplus$⟨pyridinium-F⟩ I$^\ominus$ |
| 2 | CH$_3$CH$_2$—N$^\oplus$⟨pyridinium-CH$_3$⟩ | CH$_3$CH$_2$—N$^\oplus$⟨pyridinium-F⟩ BF$_4^\ominus$ |
| 3 | (CH$_3$)$_2$CH—N$^\oplus$⟨pyridinium-CH$_3$⟩ | (CH$_3$)$_2$CH—N$^\oplus$⟨pyridinium-F⟩ $^\ominus$O.SO$_2$—⟨C$_6$H$_4$⟩—CH$_3$ |
| 4 | CH$_2$=CH.CH$_2$—N$^\oplus$⟨pyridinium-CH$_3$⟩ | CH$_2$=CHCH$_2$—N$^\oplus$⟨pyridinium-F⟩ $^\ominus$O.SO$_2$—⟨C$_6$H$_4$⟩—CH$_3$ |

TABLE I-continued

[Core structure shown at top: β-lactam with hydroxyethyl group and S-CH2CH2-NHR'⊕ side chain with COO⊖]

| Compound | R' | Remarks |
|---|---|---|
| 5 | 4-methyl-2-methyl-N-methylpyridinium | 4-fluoro-2-methyl-N-methylpyridinium BF4⊖ |
| 6 | 2,4,6-trimethyl-N-methylpyridinium | 4-fluoro-2,6-dimethyl-N-methylpyridinium ⊖PF6 |
| 7 | 4-methyl-N-(methoxymethyl)pyridinium | 4-fluoro-N-(methoxymethyl)pyridinium Br⊖ |
| 8 | 4-methylpyridinium (NH⊕) | From Compound 7 by reaction with (a) ISi(CH3)3 then (b) H2O. |
| 9 | N-methyl-2-(p-nitrobenzyloxycarbonyl)-4-methylpyridinium | 4-fluoro-N-methyl-2-(p-nitrobenzyloxycarbonyl)pyridinium BF4⊖ |
| 10 | N-methyl-2-carboxylato-4-methylpyridinium COO⊖M⊕ | from compound 9 by catalytic hydrogenolysis at pH 7 |
| 11 | N-methyl-3-(p-nitrobenzyloxycarbonyl)-4-methylpyridinium | 4-chloro-N-methyl-3-(p-nitrobenzyloxycarbonyl)pyridinium BF4⊖ |
| 12 | N-methyl-3-carboxylato-4-methylpyridinium COO⊖M⊕ | from compound 11 by catalytic hydrogenolysis at pH 7 |
| 13 | N-(p-nitrobenzyloxycarbonylmethyl)-4-methylpyridinium O2N-C6H4-CH2OOC.CH2-N⊕ | 4-chloro-N-(p-nitrobenzyloxycarbonylmethyl)pyridinium Br⊖ |
| 14 | N-(carboxylatomethyl)-4-methylpyridinium M⊕⊖OOCCH2-N⊕ | from compound 13 by catalytic hydrogenolysis at pH 7 |

TABLE I-continued

[Structure: carbapenem core with OH, S-CH₂CH₂-NHR'⊕ side chain and COO⊖]

| Compound | R' | | Remarks |
|---|---|---|---|
| 15 | [4-methyl-3-chloro-N-methylpyridinium] | [4-methyl-3-chloro-5-fluoro-N-methylpyridinium] BF₄⊖ | |
| 16 | [4-methyl-3-methoxy-N-methylpyridinium] | [4-methyl-3-methoxy-5-fluoro-N-methylpyridinium] BF₄⊖ | |
| 17 | [4-methyl-N-phenylpyridinium] | [4-methyl-5-fluoro-N-phenylpyridinium] ⊖OSO₂-C₆H₄-CH₃ | |
| 18 | [4-methyl-N-hydroxypyridinium] HO | [4-methyl-5-fluoro-N-oxide pyridinium] ⊖O | |
| 19 | [4-methyl-N-methoxypyridinium] CH₃O | [4-methyl-5-fluoro-N-methoxypyridinium] CH₃O, BF₄⊖ | |
| 20 | [4-methyl-N-aminopyridinium] NH₂ | | from compound 8 by reaction with H₂N.O.SO₃H |
| 21 | [4-methyl-3-SO₃⊖M⊕-N-methylpyridinium] | [4-methyl-5-fluoro-3-SO₃CH₃-N-methylpyridinium] ⊖BF₄⊕ | and subsequent hydrolysis at pH = 9 and titration to pH = 7 |
| 22 | [4-methyl-3-NH₂-N-methylpyridinium] | [4-methyl-5-fluoro-3-NH.CO.OCH₂-C₆H₄-NO₂-N-methylpyridinium] BF₄⊖ | and subsequent catalytic hydrogenolysis at pH 7 |

TABLE I-continued

[Structure: β-lactam with OH-CH(CH3)- substituent, S-CH2CH2-NHR'⁺ side chain, COO⁻]

| Compound | R' | Remarks |
|---|---|---|
| 23 | [N-methylpyridinium with NH2] | [4-F, 2-NH.CO.OCH2-C6H4-NO2 N-methylpyridinium, BF4⁻] and subsequent catalytic hydrogenolysis at pH 7 |
| 24 | [N-methyl-4-methylpyridinium with O.CO.CH2-C6H4-NO2] | [4-F N-methylpyridinium with O.CO.CH2-C6H4-NO2, PF6⁻] |
| 25 | [N-methylpyridinium with OH] | from compound 24 by catalytic hydrogenolysis at pH 7 |
| 26 | [N-methyl-4-methylpyridinium with OCO.CH2-C6H4-NO2] | [4-F N-methylpyridinium with OCO.CH2-C6H4-NO2, PF6⁻] |
| 27 | [N-methyl-4-methyl-2-pyridone] | from compound 26 by catalytic hydrogenolysis at pH 7, then isolating the product as the —COO⁻M⁺ salt. |
| 28 | [N-methyl-4-methylpyridinium with CH2OCH3] | [4-F N-methylpyridinium with CH2OCH3, I⁻] |
| 29 | [N-methyl-4-methylpyridinium with CO.NH2] | [4-F N-methylpyridinium with CO.NH2, BF4⁻] |
| 30 | [N-methyl-4-methylpyridinium with CO.NH2] | [4-F N-methylpyridinium with CO.NH2, BF4⁻] |

TABLE I-continued

Structure: (hydroxyethyl carbapenem core)—S—CH$_2$CH$_2$—NHR'$^{\oplus}$, with COO$^{\ominus}$

| Compound | R' | Remarks |
|---|---|---|
| 31 | pyridinium (N-CH$_3$, 2-NHCONH$_2$) | 4-F pyridinium (N-CH$_3$, 2-NH.CO.NH$_2$), BF$_4^{\ominus}$ |
| 32 | CH$_3$COCH$_2$-pyridinium (4-methyl) | CH$_3$COCH$_2$-pyridinium (4-Cl), Br$^{\ominus}$ |
| 33 | PhCOCH$_2$-pyridinium (4-methyl) | PhCOCH$_2$-pyridinium (4-Cl), Br$^{\ominus}$ |
| 34 | furfuryl-pyridinium (4-methyl) | furfuryl-pyridinium (4-Cl), Br$^{\ominus}$ |
| 35 | M$^{\oplus\ominus}$OOC–C$_6$H$_4$–CH$_2$–pyridinium (4-methyl) | O$_2$N–C$_6$H$_4$–CH$_2$OOC–C$_6$H$_4$–CH$_2$–pyridinium (4-F), Br$^{\ominus}$; and subsequent catalytic hydrogenolysis at pH 7 |
| 36 | HO–C$_6$H$_4$–CH$_2$–pyridinium (4-methyl) | from NH$_2$–C$_6$H$_4$–CH$_2$CO.O–C$_6$H$_4$–CH$_2$–pyridinium (4-F), Br$^{\ominus}$; and subsequent catalytic hydrogenolysis at pH 7 |
| 37 | 3,4-(CH$_3$O)$_2$C$_6$H$_3$–CH$_2$–pyridinium (4-methyl) | 3,4-(CH$_3$O)$_2$C$_6$H$_3$–CH$_2$–pyridinium (4-F), Br$^{\ominus}$ |
| 38 | PhCH$_2$–pyridinium (2-COOCH$_2$–C$_6$H$_4$–NO$_2$) | PhCH$_2$–pyridinium (4-F, 2-COOCH$_2$–C$_6$H$_4$–NO$_2$), Br$^{\ominus}$ |

TABLE I-continued
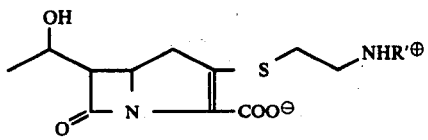
| Compound | R' | Remarks |
|---|---|---|
| 39 | 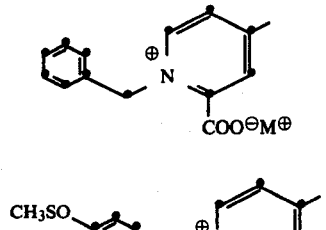 | from compound 38 by catalytic hydrogenolysis at pH 7. |
| 40 | 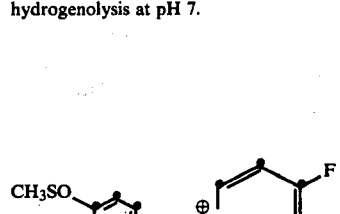 | |
| 41 | 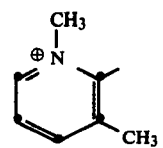 | by reaction in anhydrous DMF with diethylisopropylamine as base |
| 42 | 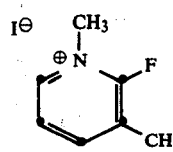 | |
| 43 | 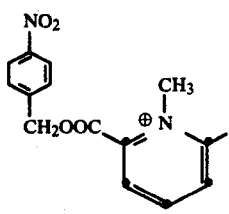 | from compound 42 by catalytic hydrogenolysis at pH 7 |
| 44 | 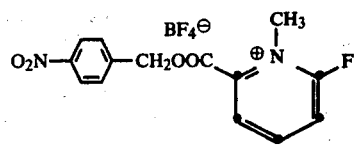 | |
| 45 | 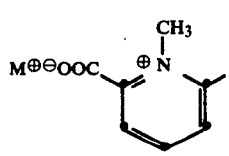 | from compound 44 by catalytic hydrogenolysis at pH 7 |
| 46 | 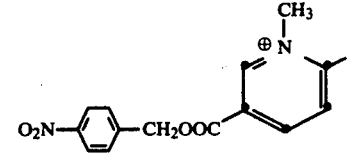 | |

TABLE I-continued

[Structure: core bicyclic β-lactam with OH-CH(CH3)- substituent, S-CH2CH2-NHR'⊕ group, and COO⊖]

| Compound | R' | Remarks |
|---|---|---|
| 47 | 3-chloro-2-methyl-1-methylpyridinium | BF4⊖; 3-chloro-6-fluoro-2-methyl-1-methylpyridinium |
| 48 | 5-chloro-2-methyl-1-methylpyridinium | BF4⊖; 5-chloro-6-fluoro-2-methyl-1-methylpyridinium |
| 49 | 2,6-dimethyl-1-methylpyridinium | BF4⊖; 6-fluoro-2,6-dimethyl-1-methylpyridinium |
| 50 | 2-methyl-1-(methoxymethyl)pyridinium | 2-methyl-6-fluoro-1-(methoxymethyl)pyridinium; Br⊖ |
| 51 | pyridinium (N-H) | from compound 50 by reaction with (a) ISi(CH3)3 then (b) H2O |
| 52 | 1-hydroxy-2-methylpyridinium | 1-oxy-6-fluoro-2-methylpyridinium |
| 53 | 1-methoxy-2-methylpyridinium | BF4⊖; 1-methoxy-6-fluoro-2-methylpyridinium |
| 54 | 1-amino-2-methylpyridinium | from compound 51 by reaction with H2NO·SO3H |
| 55 | O2N-C6H4-CHOOC·CH2-N-pyridinium (2-methyl) | O2N-C6H4-CHOOC·CH2-N-pyridinium (6-fluoro-2-methyl); Br⊖ |

TABLE I-continued

[Structure: β-lactam core with OH-CH(CH3)- substituent, S-CH2CH2-NHR'⊕ side chain, and COO⊖ group]

| Compound | R' | Remarks |
|---|---|---|
| 56 | [N-methylenepyridinium with M⊕OOC.CH2 group] | from compound 55 by catalytic hydrogenolysis at pH 7 |
| 57 | [N-CH3 pyridinium with H2N- substituent] | [BF4⊖; N-CH3 fluoropyridinium with O2N-C6H4-CH2O.CONH- group] and subsequent catalytic hydrogenolysis at pH 7 |
| 58 | [N-CH3 pyridinium with M⊕⊖O3S- group] | [BF4⊖; N-CH3 chloropyridinium with CH3OSO2- group] and subsequent hydrolysis at pH 9 and titration to pH 7 |
| 59 | [N-benzyl pyridinium] | [Br⊖; N-(methylbenzyl) fluoropyridinium] |
| 60 | [N-(4-hydroxybenzyl) pyridinium] | [Br⊖; N-(4-(O2N-C6H4-CH2COO)-benzyl) fluoropyridinium] and subsequent catalytic hydrogenolysis at pH 7 |
| 61 | [N-(3-(O2N-C6H4-CH2OOC)-benzyl) pyridinium] | [Br⊖; N-(3-(O2N-C6H4-CH2OOC)-benzyl) fluoropyridinium] |

TABLE I-continued

[Structure shown at top of table: β-lactam core with OH, CH₃, S-CH₂CH₂-NHR'⊕ side chain, and COO⊖ group]

| Compound | R' | Remarks |
|----------|-----|---------|
| 62 | [4-(M⊕⊖OOC)-benzyl-CH₂-N⊕(2-methylpyridinium)] | from compound 61 by catalytic hydrogenolysis at pH 7 |
| 63 | [furfuryl-CH₂-N⊕(2-methylpyridinium)] | [furfuryl-CH₂-N⊕(2-methyl-6-fluoropyridinium)] Br⊖ |
| 64 | [3,5-dichlorobenzyl-CH₂-N⊕(2-methylpyridinium)] | [3,5-dichlorobenzyl-CH₂-N⊕(2-methyl-6-fluoropyridinium)] Br⊖ |
| 65 | [4-pyridyl-N⊕(2-methylpyridinium)] | [4-pyridyl-N⊕(2-methyl-6-fluoropyridinium)] ⊖OSO₂-C₆H₄-CH₃ |
| 66 | [O₂N-C₆H₄-CH₂OOC-pyridyl-N⊕(2-methylpyridinium)] | [O₂N-C₆H₄-CH₂OOC-pyridyl-N⊕(2-methyl-6-fluoropyridinium)] ⊖OSO₂-C₆H₄-CH₃ |
| 67 | [M⊕⊖OOC-pyridyl-N⊕(2-methylpyridinium)] | from compound 66 by catalytic hydrogenolysis at pH 7 |
| 68 | [N-methyl-2-methyl-pyrimidinium⊕] | [N-methyl-2-fluoro-pyrimidinium⊕] BF₄⊖ |

TABLE I-continued

[Structure: core bicyclic β-lactam with OH-CH(CH3)- substituent, S-CH2-CH2-NHR'⊕ side chain, and COO⊖ group]

| Compound | R' | Remarks |
|---|---|---|
| 69 | [N-ethyl pyrimidinium-type ring with CH2CH3] | BF4⊖ [fluorinated analog shown] |
| 70 | [N-methyl pyrimidinium ring] | ⊖OSO2-C6H4-CH3 [fluorinated analog] |
| 71 | [N-benzyl pyrimidinium ring] | ⊖OSO2-C6H4-CH3 [fluorinated analog] |
| 72 | [N-benzyl pyrimidinium ring, isomer] | ⊖OSO2-C6H4-CH3 [fluorinated analog] |
| 73 | [N-phenyl pyrimidinium ring] | ⊖OSO2-C6H4-CH3 [fluorinated analog] |
| 74 | [N-methyl thiazolium ring] | BF4⊖ [2-fluoro analog] |
| 75 | [N-methyl-4-phenyl thiazolium] | BF4⊖ [2-fluoro analog] |
| 76 | [N-ethyl-5-methyl thiazolium] | BF4⊖ [2-fluoro analog] |
| 77 | [N-ethyl isoxazolium with phenyl] | BF4⊖ [fluorinated analog] |

TABLE I-continued

Structure: 6-(1-hydroxyethyl)-3-[(2-(NHR'⊕)ethyl)thio]-7-oxo-1-azabicyclo[3.2.0]hept-2-ene-2-carboxylate

| Compound | R' | Remarks |
|---|---|---|
| 78 | N-ethyl-3,5-dimethylisoxazolium | BF₄⁻; fluoro derivative |
| 79 | N-ethyl-3-methylisoxazolium | BF₄⁻; fluoro derivative |
| 80 | 1,3-dimethyl-2-methylbenzimidazolium | BF₄⁻; 2-fluoro-1,3-dimethylbenzimidazolium |
| 81 | 5-methoxy-1,3-dimethyl-2-methylbenzimidazolium | BF₄⁻; 2-fluoro-5-methoxy-1,3-dimethylbenzimidazolium |
| 82 | 3-ethyl-2-methylbenzoxazolium | BF₄⁺; 2-fluoro-3-ethylbenzoxazolium |
| 83 | 3-methyl-2-methylbenzoxazolium | BF₄⁻; 2-fluoro-3-methylbenzoxazolium |
| 84 | 3-methyl-2-methylbenzothiazolium | BF₄⁻; 2-fluoro-3-methylbenzothiazolium |
| 85 | N-cyano-4-methylpyridinium | 4-fluoro derivative, ⁻OSO₂-C₆H₄-CH₃ |
| 86 | N-cyano-2-methylpyridinium | 2-fluoro derivative, ⁻OSO₂-C₆H₄-CH₃ |

TABLE I-continued

[Structure: β-lactam core with OH, CH₃, S-CH₂CH₂-NHR'⊕, and COO⊖ groups]

| Compound | R' | Remarks |
|---|---|---|
| 87 | [quinolinium-methyl structure] | [fluoro-quinolinium structure] Br⊖ |
| 88 | [N-methylquinolinium structure with CH₃] | [fluoro N-methylquinolinium structure with CH₃] Br⊖ |
| 89 | [bicyclic pyridinium structure] | [fluoro bicyclic pyridinium structure] ClO₄⊖ |
| 90 | [bicyclic pyridinium structure] | [fluoro bicyclic pyridinium structure] ⊖OSO₂—C₆H₄—CH₃ |
| 91 | [bicyclic pyridinium structure] | [fluoro bicyclic pyridinium structure] ⊖OSO₂—C₆H₄—CH₃ |
| 92 | CH₃OCH₂—[pyrimidinium structure] | CH₃OCH₂—[fluoro pyrimidinium structure] Br⊖ |
| 93 | H—[pyrimidinium structure with F] | prepared from compound 92 by reaction with (a) ISi(CH₃)₃ then (b) H₂O |
| 94 | NC—[benzyl-pyridinium structure] | NC—[benzyl-fluoropyridinium structure] Br⊖ |
| 95 | (CH₃)₂N—[benzyl-pyridinium structure] | (CH₃)₂N—[benzyl-fluoropyridinium structure] Br⊖ |

TABLE I-continued

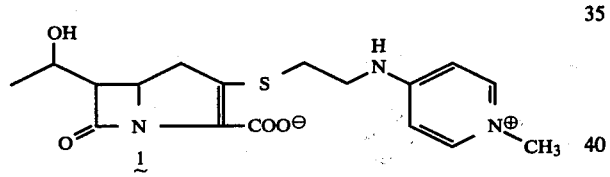

| Compound | R' | Remarks |
|---|---|---|
| 96 | (phenethyl-pyridinium, methyl) | (phenethyl-pyridinium, F) ⊖OTs |
| 97 | Cl₃C.CH₂.O.CH₂—⊕N(methylpyridinium) | Cl₃C.CH₂.OCH₂—N(fluoropyridinium) Br⊖ |
| 98 | F₃C.CH₂.O.CH₂—⊕N(methylpyridinium) | F₃C.CH₂.O.CH₂—⊕N(fluoropyridinium) Br⊖ |
| 99 | (benzyloxyethyl-methylpyridinium) | (benzyloxyethyl-fluoropyridinium) Br⊖ |

EXAMPLE 5

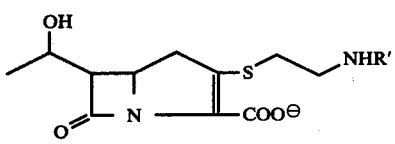

Preparation of Pharmaceutical Compositions

One such unit dosage form comprises a blend of 120 mg of 1 with 20 mg of lactose and 5 mg of magnesium stearate which is placed in a No. 3 gelatin capsule. Similarly, by employing more of the active ingredient and less lactose, other dosage forms can be prepared; should it be necessary to mix more than 145 mg. of ingredients together, larger capsules may be employed. Equivalently, compressed tablets and pills can be prepared. The following examples are further illustrative of the preparation of pharmaceutical formulations:

| TABLET | PER TABLET |
|---|---|
| Compound 1 | 125 mg. |
| Dicalcium Phosphate | 200 mg. |
| Cornstarch, U.S.P. | 6 mg. |
| Lactose, U.S.P. | 200 mg. |
| Magnesium Stearate | 270 mg. |

The above ingredients are combined and the mixture is compressed into tablets, approximately 0.5 inch in diameter each weighing 800 mg.

What is claimed is:

1. A compound having the structural formula:

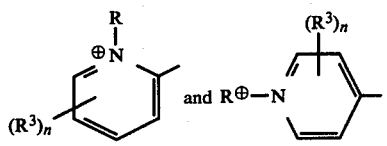

or a pharmaceutically acceptable salt or ester thereof wherein:

R' is selected from the group consisting of:

$$\underset{(R^3)_n}{\overset{R}{\underset{\oplus N}{\bigcirc}}} \quad \text{and} \quad R^{\oplus}-N\underset{(R^3)_n}{\bigcirc}$$

wherein:

R is hydrogen, alkyl having from 1–6 carbon atoms, substituted alkyl having from 1–6 carbon atoms wherein the substituent is chloro, fluoro, hydroxyl, alkoxyl ($C_{1-6}$), carboxyl, amino, sulfo and mono- and dialkylamino wherein each alkyl has 1–6 carbon atoms substituted and unsubstituted phenylaklkyl and phenylalkenyl having 7–12 carbon atoms wherein the substituent is selected from chloro, fluoro, carboxyl, amino, cyano, hydroxyl and sulfo;

$R^3$ is chloro, fluoro, hydroxyl, carboxyl, sulfo, cyano, amino, mono- and diloweralkylamino, loweralkoxyl, alkyl having from 1–6 carbon atoms, substituted alkyl having 1–6 carbon atoms wherein the substituent is carboxyl, cyano, alkoxyl having 1–6 carbon atoms, phenyl and phenyloxy; and n is an integer selected from 0 to 3.

2. A compound according to claim 1 wherein n is 0 or 1; and R is hydrogen or substituted or unsubstituted alkyl or phenylalkyl.
3. A compound according to claim 2 wherein R' is selected from the group consisting of:
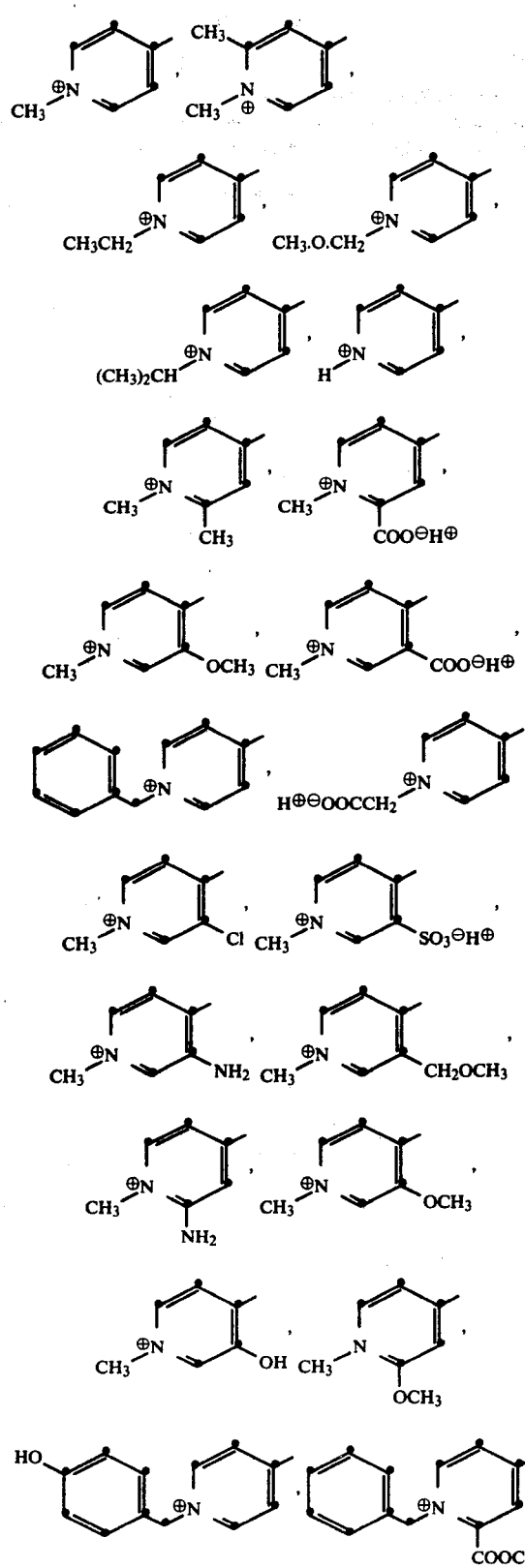
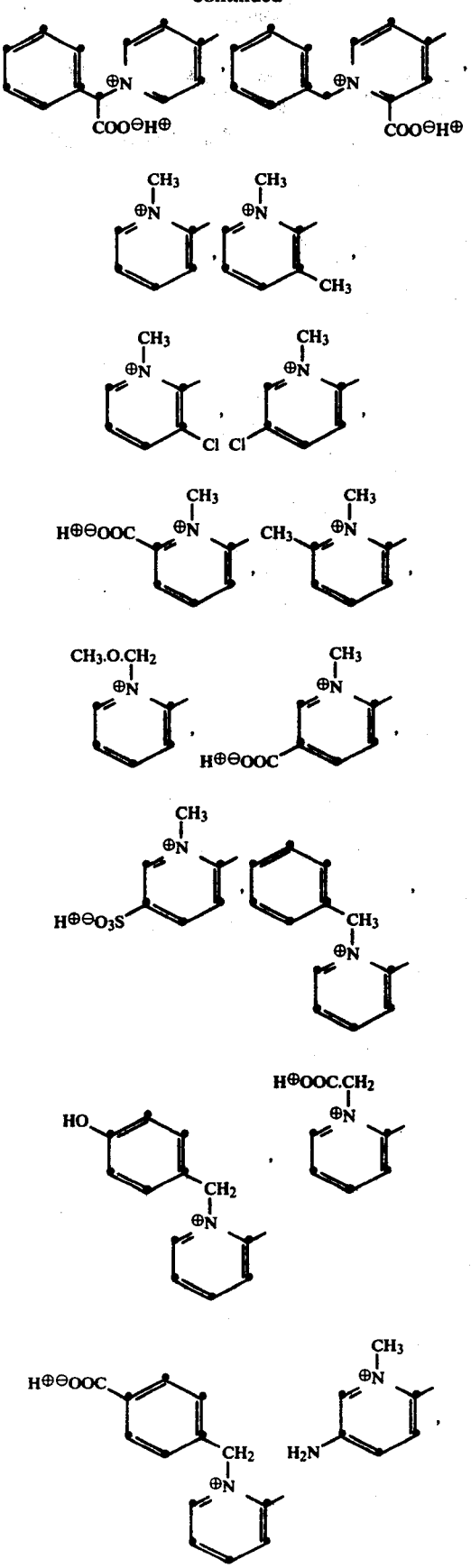

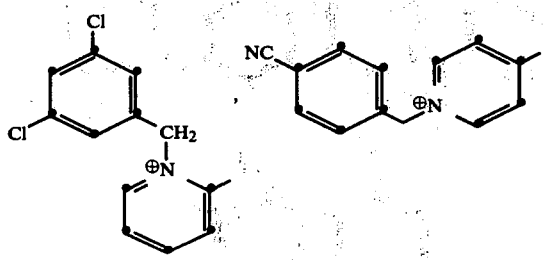
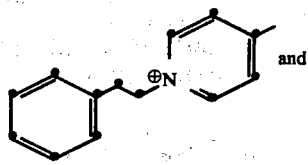
4. An antibiotic pharmaceutical composition comprising a therapeutically effective amount of a compound according to claim 1 and a pharmaceutical carrier therefor.
* * * * *